United States Patent
Staggs (10) Patent No.: US 6,593,371 B1
(45) Date of Patent: Jul. 15, 2003

(54) TREATMENT FOR WART AND RELATED DISORDERS

(76) Inventor: Jeff J. Staggs, 1285 E. Goldsmith Dr., Highlands Ranch, CO (US) 80126

( * ) Notice: Subject to any disclaimer, the term of this patent is extended or adjusted under 35 U.S.C. 154(b) by 0 days.

(21) Appl. No.: 09/571,644

(22) Filed: May 15, 2000

Related U.S. Application Data (63) Continuation-in-part of application No. PCT/US93/04763, filed on May 19, 1993.

(51) Int. Cl.$^7$ .......................... A61K 31/16; A61K 31/70
(52) U.S. Cl. .......................................... 514/627; 514/31
(58) Field of Search ................................... 514/627, 31

(56) References Cited

U.S. PATENT DOCUMENTS 4,180,058 A * 12/1979 Brem .......................... 128/1 R
6,063,381 A * 5/2000 Staggs ..................... 424/195.1

* cited by examiner

*Primary Examiner*—Kevin E. Weddington (57) ABSTRACT

A novel treatment for wart and related disorders such as papillomas derived from extracts of pepper, ginger, and related plant species containing vanillyl (FIG. 3), and piperidine (FIG. 7) ring structures typical of the pungent principals found in pepper, and ginger. The pepper extracts, which also possess antifungal properties are demonstrated in the topical treatment of warts.

38 Claims, 7 Drawing Sheets

PHENOL C$_6$H$_5$OH

FIGURE 1

ORTHO - METHOXYPHENOL CH$_3$OC$_6$H$_4$OH

FIGURE 2

VANILLYL (CH$_3$O) (OH) C$_6$H$_3$ - CH$_2$

FIGURE 3

3-METHOXY-4-HYDROXYBENZYLAMINE
(CH$_3$O) (OH) C$_6$H$_3$-CH$_2$-NH$_2$

FIGURE 4 where R is an organic hydrocarbon group

VANILLYLAMIDE (CH$_3$O)(OH)C$_6$H$_3$ - NH - R

FIGURE 5

R - CO - (CH$_2$)$_4$ - CH = CH - CH - (CH$_3$)$_2$                 CAPSAICIN
R - CO - (CH$_2$)$_6$ - CH - (CH$_3$)$_2$                      DIHYDRO    "
R - CO - (CH$_2$)$_5$ - CH - (CH$_3$)                         NORDIHYDRO   "
R - CO - (CH$_2$)$_9$ - CH - (CH$_3$)$_2$                      HOMODIHYDRO "
R - CO - (CH$_2$)$_5$ - CH = CH - CH (CH$_3$)$_2$        HOMO         "
R - CO - (CH$_2$)$_7$ - CH$_3$           NONANOIC ACID VANILLYLAMIDE
R - CO - (CH$_2$)$_8$ - CH$_3$           DECANOIC ACID VANILLYLAMIDE

CAPSAICINOIDS

FIGURE 6

PIPERIDINE (CH$_2$)$_5$NH

FIGURE 7

PUNGENT ALKALOIDS PRINCIPALS OF PEPPER

FIGURE 8

EUGENOL C$_{10}$H$_{12}$O$_2$

FIGURE 9

CURCUMIN C$_{21}$H$_{20}$O$_6$

FIGURE 10

GINGEROL  SHOGAOL $C_{17}H_{24}O_3$

(where n = 4, 6, or 8)

PARADOL  ZINGERONE $C_{11}H_{14}O_3$

GINGEROLS

FIGURE 11

RESINIFERATOXIN

TINYATOXIN

TREATMENT FOR WART AND RELATED DISORDERS

PRIORITY INFORMATION

This is a continuation-in-part of continuation-in-part application PCT/US93/04763 International Filing date May 19, 1993, which is also U.S. PCT National Stage Application Ser. No. 08/338 489 filed Mar. 18, 1997 which became U.S. Pat. No. 6,063,381 all of which claim priority from U.S. National application Ser. No. 07/886,640 filed May 21, 1992 now abandoned

TECHNICAL FIELD

The invention relates to a novel treatment for wart and related disorders such as papillomas derived from extracts of pepper and ginger and chemically related species.

BACKGROUND ART

Warts, or verrucae infect man and animal alike. More than 80 related strains of papillomavirus (HPV) have been identified as the cause. It is estimated than 40 million Americans have some form of HPV infection.

Most warts are harmless, but may also harbor bacterial infections. Still other may cause cancer of the cervix, vagina, vulva, anus, penis, mouth, throat, or esophagus.

Warts affect all age groups, but are most common in children. Almost everyone has had common warts. These infect the fingers, around nails, knees, face, scalp, and may spread to other areas including the mouth.

Plantar warts develop on the sole of the foot, causing pain, particularly while walking and thickening of the surrounding skin. Plantar warts are difficult to cure.

Filiform warts form long, narrow, small growths on eyelids, face, neck, or lips.

Flat warts (more common in children and young adults) form smooth yellow-brown spots usually on the face.

Seborrheic warts, though not caused by a virus are found most commonly on the face of the aged.

Genital warts are transmitted sexually, infecting the vulva, vaginal wall, cervix, and areas around the vagina In men, the penis and surrounding areas may be infected. Also a site of infection is the area around the anus and in the rectum more common in homosexual men, and in women who engage in anal sex. Some types of genital warts emit foul smelling secretions. The mouth and throat are also an area of infection and transmission as a result of oral sex with infected genitalia. Genital warts return frequently and require repeated treatment. They are highly contagious, with an estimated 1 million new cases occurring each year in the U.S. Sites of infection including vagina, cervix, uterus, penis, rectum, mouth, throat ect, are at increased risk for developing cancer. Immunocompromised patients with AIDS, cancer, diabetes, and recipients of organ transplant medication are most susceptible to HPV, as well as other infections.

Warts are unsightly, causing revulsion, embarrassment in addition to itch, foul odor, pain discomfort, and increased cancer risk. Prior art treatments are expensive, prolonged, and often ineffective. Even wealthy sufferers, with the best health care available are hardly much better off than the poorest of the world with regard to wart afflictions.

The prior art acid peel method requires several weeks or months of repeated daily applications hoping to soften the wart enough to allow it to be peeled off This method often burns the surrounding healthy skin and frequently fails.

Physician administered nitrogen freezing, electrodesiccation, curettage, laser, and stronger acid treatments are effective to destroy the wart, but often leave a scar in place of the wart. Treatment is expensive, requiring administration by a physician, and often requires follow-up. In spite of these measures, the wart returns about one-third of the time, or new ones crop up around the edges of the old one. These poor results are obtained at a cost of several hundred dollars.

The failure of prior art medications to produce an effective, reasonably priced wart treatment has several negative consequences. Patients cannot get adequate relief The high cost of treatment adds further to the already exorbitant cost of healthcare borne by employers, government, and ultimately the patient through added medical bills, increased insurance premiums and higher taxes. Repeated physician visits reduce worker productivity, and leisure time.

Unresolved wart cases with cancer causing HPV may result in severe illness, or loss of life for many, in addition to the much greater medical costs associated with cancer treatment. These misfortunes are multiplied as cancer causing HPV strains are spread to others. At particular disadvantage are low-income individuals without healthcare insurance who cannot afford cancer treatment, and are most likely to perish as a result.

Prior art wart treatments lack the effectiveness necessary to treat the problem sufficient to attract consumer appeal and secure product profitability, and success for drug companies. They lack economic feasibility for development of low cost treatments for the poor of industrialized countries, developing countries, and similar products for livestock, companion animal, and other veterinary uses to the detriment of patient and supplier alike.

Today, more than every before, the importance of having medications that are not only safe, and effective, but cost effective as well, is becoming critical to the preservation of our way of life. Escalating health care costs in the United States are causing real hardship on the middle and lower income Americans as 1 in 6 cannot afford health care insurance. A greater share of the household budget otherwise spent on housing, college education, retirement, entertainment, and consumer goods must instead go to cover health care costs. The standard of living is lowered as capital is taken from industries that provide employment, and create tax revenues. The national debt continues to soar as increasing numbers of citizens are excluded from adequate medical care. Is health care at the risk of economic rum a real benefit to society?

DISCLOSURE OF INVENTION

Several objects and advantages of my invention include an improved treatment for wart infections of unparalleled effectiveness. A treatment that saves the misery of millions of sufferers, is low in toxicity, low in cost, safe, leaves no scarring, is affordable to the poor, and hence of broader commercial feasibility. A treatment that quickly resolves wart varieties with cancer causing potential prior to the cancerous stage to avert serious illness, loss of life, and spread of the infection to other parts of the body, and to other persons, and eliminates the need for costly cancer treatment. A treatment that saves billions of dollars annually in patient productivity, healthcare costs, and capable of becoming a model for demonstrated savings in commercial healthcare, and government sponsored programs such as Medicare, and Medicaid. An economically feasible veterinary wart treatment for livestock, pets, companion, and other animals of broadened commercial appeal. An important reseach tool applicable toward other related tumors, neoplasms, growths, papillomas, cancers, and viral disorders.

I have discovered that pepper, and chemically related compounds, and species of plants contain active agents of unparalleled effectiveness in the treatment of wart infections. These agents administered in a wide range of concentrations within commonly used drug vehicles and carriers such as a lotion, drops, tincture, and other vehicles with a level of effectiveness truly generations ahead of currently available prior art wart treatments.

Various types of warts including common warts, plantar warts, filiform warts, flat warts, genital warts, seborrheic warts and others may be completely healed in as few as a single topical treatment with this medication. This treatment requires no follow up, no attending physician, and leaves no scarring. Lower dose treatments produce cure in as few as half a dozen applications of my medicine rather than many scores of applications over a period of many weeks usually required by prior art wart medications that often do not cure.

Currently available prior art over the counter topical wart treatments containing salicylic acid usually require twelve weeks of daily multiple treatments. The time, and inconvenience involved in making repeated applications with meager results add further to the misery and discomfort of the disease. The weak therapeutic action of prior art over-the-counter treatments is often insufficient to produce adequate results. Often, the disorder must be treated surgically by a physician with scarring and failure to cure a common outcome.

Physician administered wart treatments are the most expensive, costing several hundred dollars with usually disappointing results. Nitrogen freezing, electrodesiccation, curretage, laser, and stronger acid treatments do little more. than mutilate the site of the wart, leaving a scar in place of the wart, and often damage surrounding healthy skin. In spite of these measures, the wart returns in about a third of the cases, or new warts emerge around the site of the old ones. In addition to being ineffective, these treatments are burdensome to healthcare costs and services, and result in loss of patient productivity and free time.

With the current invention, physician administered treatments for warts with the excessive cost, inconvenience, and poor result are in most cases a thing of the past.

Pepper extracts appear to possess multiple therapeutic actions in addition to direct antiviral/antimicrobial action. Case observations suggest general healing (vulnerary), keratolytic, immunostimulation and modulation, adjuvant, drug delivery, and prophylactic properties beyond direct antimicrobial. Though not tested to date for antiviral activity in vitro, antiviral, and other antimicrobial properties are believed to exist. In vitro antifungal screens prove proportionally increased potency against terminal drug resistant fungi strains in addition to unparralled effectiveness in treatment of actual disease in afflicted patients. Reference is made to U.S. Pat. No. 6,063,381 with regard to antifungal uses, and related therapeutic properties and actions that are believed to be applicable in treating papillomas, and these HPV related disorders. Antifungal medications in general, whether prior art or future art may also possess properties useful in treating wart-like disorders as disclosed here. More specifically: nystatin, amphotericin B, griseofulvin, tolnaftate, and all the "azole" derivative antifungals including, but not limited to clotimazole, miconazole, econazole, ketoconazole, along with the "triazole" class including, but not limited to such derivatives as fluconazole, terconazole, and itraconazole ect.

It appears that the high nutrient concentration found in pepper including vitamins, minerals, carotenoids, lipids, and others assist the above therapeutic effects in addition to the pungent compounds. Pepper compounds are safe, and have been in widespread use as food for thousands of years and do not induce illness, or injury as do some prior art treatments.

As a generally recognized as safe (GRAS) listed nutrient food compound, pepper medications are ideal for livestock, pet, and companion animal use in addition to human. Sytemic, as well as topical medications to control a variety of other viral disorders can be developed including feed additives to prevent disease.

The veterinary market for treatment of warts can be greatly broadened given the high effectiveness, low toxicity, and very low cost of my medication. Wart infections need no longer afflict livestock, pets, companion or other animals as before.

Prior art topical wart treatments have prevented the formation of a market for the treatment of livestock such as cattle. The cost of medicine, its very slow action, coupled with the very considerable amount of labor required to repeatedly administer the medicine, can not be justified economically. For this reason, no significant market exists within the industry for such products.

The current invention, however, enlarges the scope of product possibilities by making treatment of these disorders economically feasible.

The many therapeutic properties, and beneficial components found in pepper provide ideal prospects for treatment of other related disorders including tumors, cancers, neoplasms, and other papillomas such as polyps, and villous papillomas. These agents also provide application toward treatment of herpes simplex disorders including genital herpes, and cold sores. A systemic treatment for the more serious, and often life threatening viral disorders combining high effectiveness with a reduction in toxic side effects that too often further endanger the health of the patient is also feasible with these agents. With the steadily rising number of cancer, AIDS, and immunosuppressant drug treatment cases reported now, and anticipated for the future, pepper compounds provide an important research tool in treatments directed toward these more serious, life threatening conditions. Speedy resolution of warts with cancer causing potential is itself an important cancer preventative through elimination of the precancerous stage, and spread of the wart causing virus to other parts of the body, and to other individuals.

Commercial implementation of this topical wart treatment alone can have major impact by making affordable a certain cure to even the poorest people of both industrialized, and developing countries now excluded from care because of the high cost, and low effectiveness of prior art treatments. A complete cure that does not require an attending physician, and for less than one penny on the dollar for what is required of prior art treatments will bring relief to many millions of sufferers, rich and poor alike while expanding the consumer demand base for the product accordingly.

Full-scale implementation of these medications will save billions of dollars in Gross National Product in the treatment of wart disorders in the U.S. alone, not to mention the world.

This enhanced level of safety, effectiveness, and dramatic cost savings of this medication should serve as a model to both private managed care programs including government healthcare programs such as Medicaid, and Medicare wherein billions of dollars in medical expenditures are saved while providing the best care for recipients.

In conclusion, this novel wart treatment can save our nation and many nations of the world millions of dollars each day in medical costs, and lost productivity. It provides highly lucrative new products for commercial exploitation in the areas of human and animal health. It provides an important research tool in the prevention, and treatment of cancers, and other viral disorders including life-threatening varieties that could perhaps even save lives of man and animal alike. It makes now available speedy relief to hundreds of millions of suffers.

BRIEF DESCRIPTION OF THE DRAWINGS

FIGS. 2–13 show molecular diagrams of compounds of the current invention.

BEST MODES FOR CARRYING OUT THE INVENTION

A medicinal preparation of pepper, and its active constituents may be administered in a wide range of concentrations, and conventional drug vehicles and carriers.

The preparations described below are made from an ordinary commercial grade of ground cayenne pepper (*Capsicum frutescens*), or black pepper (*Piper nigrum*) to serve as an indicator of approximate concentration within each carrier. Their equivalents may also be prepared from pepper oleoresin, which is available. commercially in a wide range of concentrations, and pungencies. Components parts such as the pungent principals are inclusive of pure natural, synthetics, and artificial form.

The term "pepper", or "pepper compounds" are used somewhat generically, and is inclusive of related botanicals having similar constituents. For example, the Zingiberaceae family including ginger (*Zingiber officinale*), turmeric (*Curcuma longa*), cardamon (*Elettaria cardamomum*), Melegueta pepper (*Alframonum melegueta*), members of the Euphorbia genus including Euphorbia resinifera, poinsettia (*Euphorbia pulcherrima*), clove (*Eugenia aromatica*), allspice (*Pimenta officinalis*) and others such as vanilla. These also may be prepared in the same way as pepper by following the general procedures outlined in the illustration below. Higher concentrations may also be used, as many of these lack the pungency of actual pepper, and sensory irritation is less of a concern.

Included among this list of botanicals are the other members of the Solanaceae pepper family including members of the Capsicum genus with the *annuum, baccatum*, and *longum* species. These include hot peppers and sweet peppers including paprika.

Among the Piperaceae family; species of the Peperoma, and Piper genus which include the retrofractum, nigrum, and longum species. Other species of plants having similar chemistry may also be used in place of the above.

Figure 6:
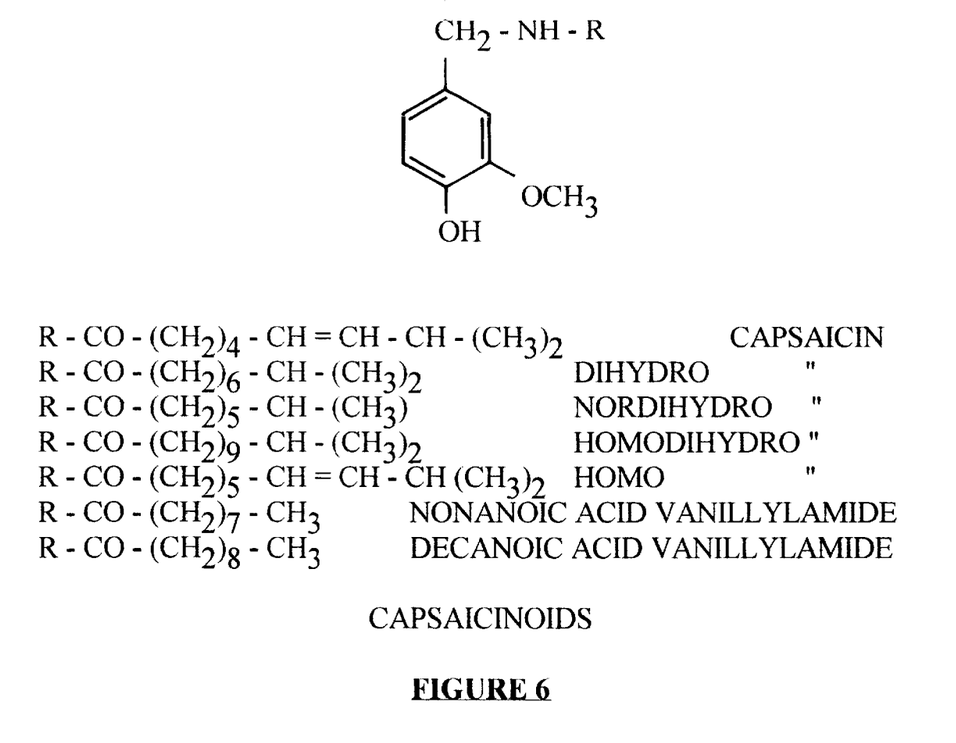
FIG. 6 is a molecular diagram of the capsaicinoids.

Variations in performance of each preparation will vary with type, concentration of extract, carrier, and solvent used in relation to organism, host, and site of infection. The scientific literature may be consulted for more detailed investigations as to chemical properties, solubility, separation, and quantitation of constituent compounds. With reference to red peppers for example, see procedures described in the article "Separation and Quantitation of Red Pepper Major Heat Principals by Reverse Phase High-Pressure Liquid Chromatography" by Patrick Hoffman et. al., in the *Journal of Agricultural Food Chemistry* 1983, Vol. 31, pages 1326–1330. The major capsaicinoids (FIG. 6) include: Capsaicin. $C_{18}H_{27}NO_3$ N-[(4-hydroxy-3-methoxyphenyl)methyl]8-methy-6-nonenamide). Dihydrocapsaicin. $C_{18}H_{29}NO_3$ (N-[(4-hydroxy-3-methoxyphenyl)methyl]-8methylnonanamide). Norcapsaicin. $C_{17}H_{25}NO_3$ (N-[(4-hydroxy-3-methoxyphenyl)methyl]7-methyl-5octenamide). Nordihydrocapsaicin. $C_{17}H_{27}NO_3$ (N-[(4-hydroxy-3-methoxyphenyl)methyl]-7-methyloctanamide. Homocapsaicin. $C_{19}H_{29}NO_3$ (N-[(4-hydroxy-3-methoxyphenyl)methyl]-9-methyl-7decenamide). Homodihydrocapsaicin. $C_{19}H_{31}NO_3$ N-[(4-hydroxy-3-methoxyphenyl)methyl]-9methyldecanamide). N-vanillyl-n-nonamide. $C_{17}H_{27}N_3$ (N-[(4-hydroxy-3-methoxyphenyl)methyl]-n-nonamide). Nonanoic acid vanillylamide. $C_{17}H_{29}NO_3$ Decanoic acid vanillylamide. $C_{18}H_{31}NO_3$ Other capsaicinoids, identified in research literature as trace elements may be used in medicinal preparations along with other analogous compounds.

Figure 1:
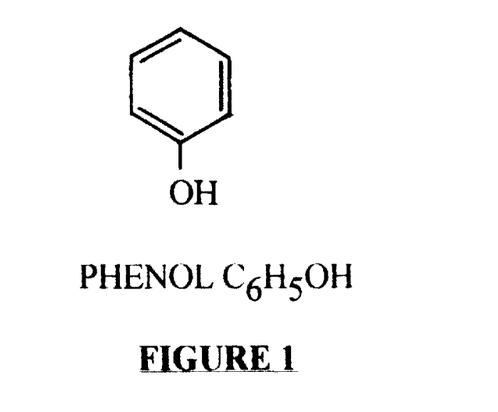
FIG. 1 is a molecular diagram of phenol.
Figure 7:
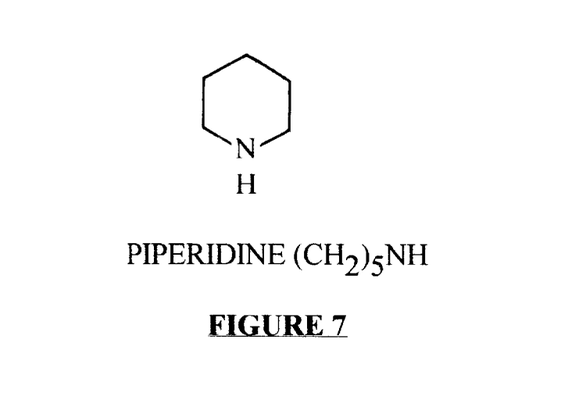
FIG. 7 is a molecular diagram of piperidine.

Capsaicinoids are acid amide derivatives of Phenol (FIG. 1). The characteristic pungent, irritating sensory effects of these compounds are typical of acid amides, whether derived from phenol, or piperidine (FIG. 7).

Phenol (FIG. 1), though lacking pungent flavor, is highly corrosive, caustic, and toxic, deriving many of its properties from its basic benzene structure. While this gives phenol certain antimicrobial properties, it is generally considered unsuitable for therapeutic use in man, and animals, due to it's and irritating effects on tissue.

Figure 2:
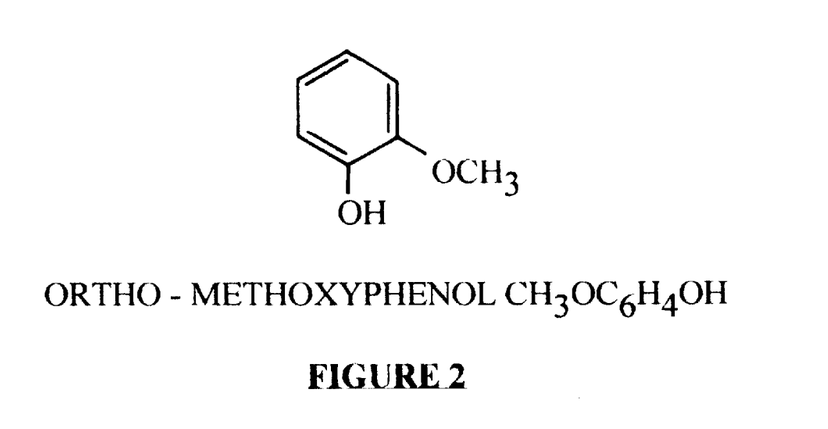
FIG. 2 is a molecular diagram of ortho-methoxyphenol.

With the addition of a methoxy group (OCH3) to phenol, methoxyphenol is formed. In the ortho position, we have ortho-methoxyphenol (FIG. 2), also known as guaiacum, an extract obtainable from trees of the Guaiacum genus. The effect of this methoxy group in part is an increase in aromacy, and a decrease in toxicity, and caustic properties otherwise existing in phenol, yet without apparent decrease in antimicrobial properties. The attachment of hydrocarbon groups to the ring structure, to form higher analogues apparently increases the antimicrobial properties of methoxyphenol, and phenol. It is presumed that the meta, or para isomers of methoxyphenol have similar properties to the ortho, in like manner to the similarities between the phenol isomers.

Figure 3:
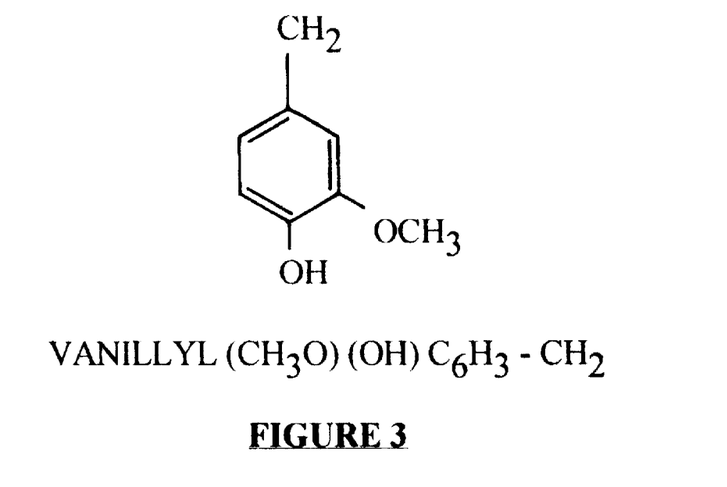
FIG. 3 is a molecular diagram of vanillyl.

The addition of the methylene group (CH2) in the para position to ortho-methoxyphenol produces vanillyl (FIG. 3). Like phenol, and methoxyphenol, it is presumed that changing the position of the methylene group to form other vanillyl isomers will produce compounds of similar, although not exact properties to that of vanillyl.

The vanillyl structure on which the capsaicinoids are constructed is also typical of the pungent principals found in ginger (Zingiberaceae) species of plants.

Figure 11:
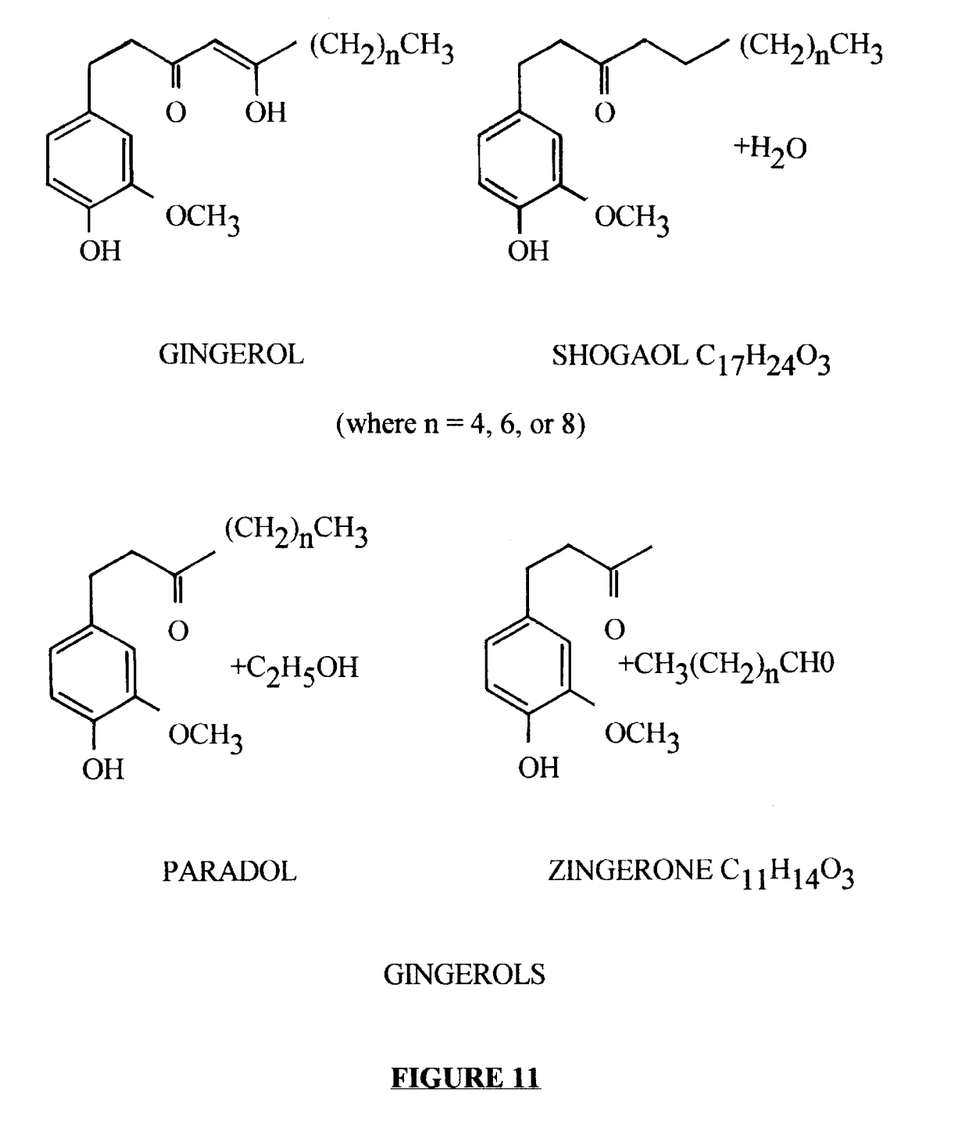
FIG. 11 is a molecular diagram of gingerol.

Collectively known as gingerol (FIG. 11): shogaol, paradol, zingerone, gingerol and other analogs, have a different side chain than the capsaicinoids, and lacking an ammonia ($NH_n$) group, are neither amines, or amides like the capsaicinoids or piperidine series. Hydrolysis of gingerols yield vanillyl, and a fatty acid side chain, both of which demonstrate like therapeutic properties to the capsaicinoid hydrolytes.

Figure 10:
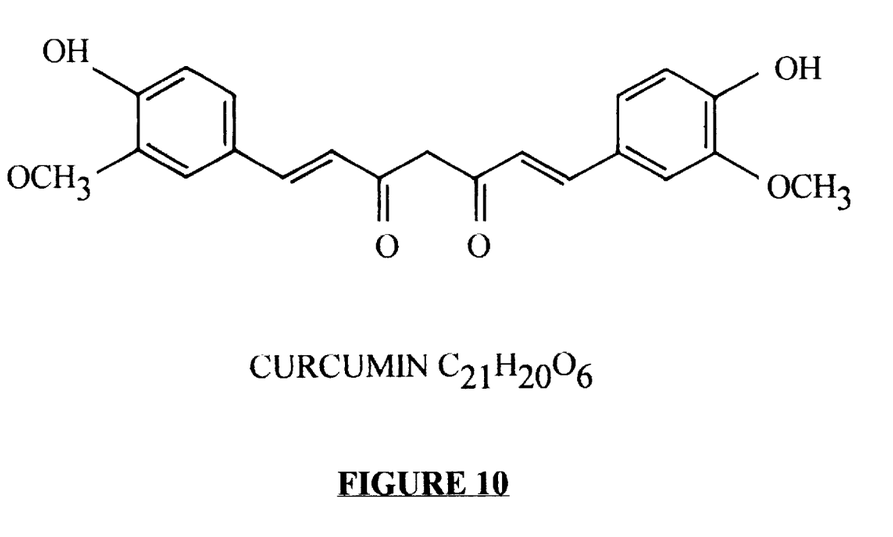
FIG. 10 is a molecular diagram of curcumin.

Also members of the ginger, or Zingiberaceae family, turmeric (*Curcuma longa* L.) contains the compound curcumin (FIG. 10), actually a vanillal derivative differing from vanillyl by one hydrogen (H) atom having an (CH) substituent, rather than a methylene (CH2) in the para position. This analog differs further with a side chain unique from the others. Cardamon, allspice, clove, black pepper, and many others contain eugenol, another vanillyl analog with yet another hydrocarbon side chain.

Figure 12:
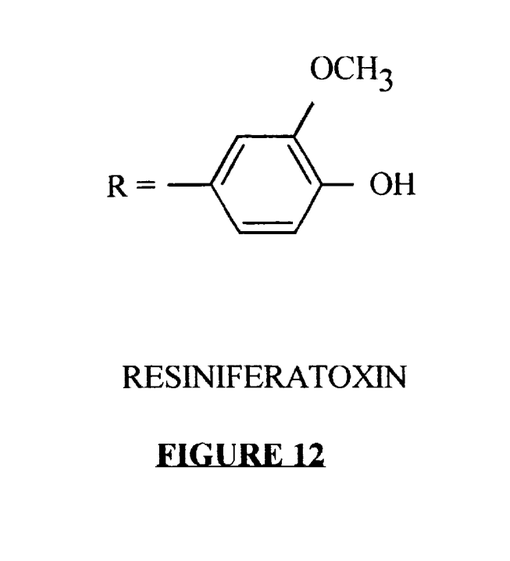
FIG. 12 is a molecular diagram of resiniferatoxin.
Figure 13:
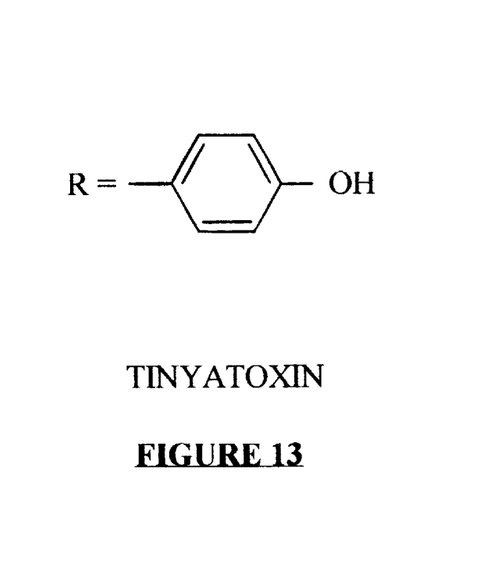
FIG. 13 is a molecular diagram of tinyatoxin.

Other botanical sources of vanilly analogs include gum euphorbium, and extract of certain species of the Euphorbia genus, which contain the capsaicin analog resiniferatoxin (FIG. 12), along with its analog tinyatoxin (FIG. 13) and others.

Figure 5:
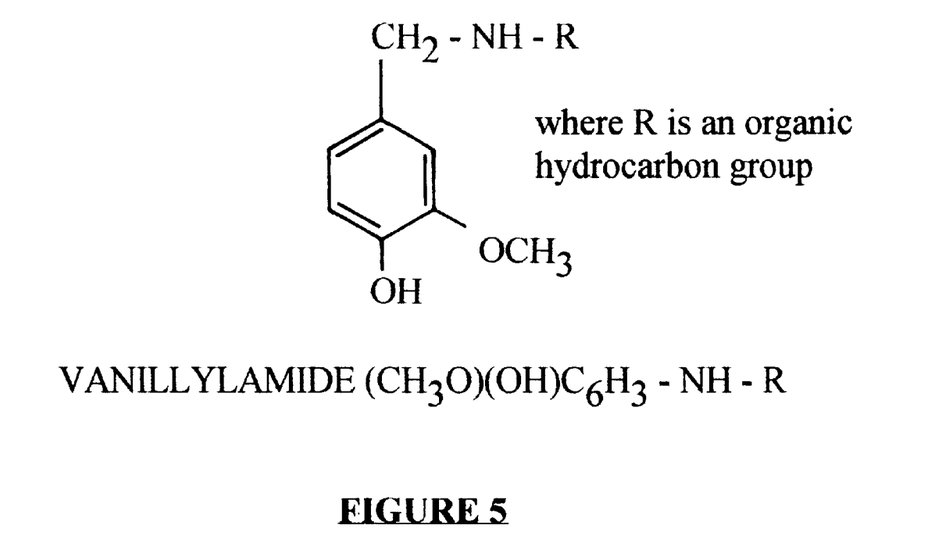
FIG. 5 is a molecular diagram of vanillylamide.

Replacement of one of the hydrogen (H) atoms of ammonia ($NH_3$), with vanillyl, and replacement of the other hydrogen (H) atom with an organic hydrocarbon group produces vanillylamide (FIG. 5). In the case of the capsaicinoids (FIG. 6), or capsaicin analogs for example, this organic hydrocarbon group is a chain acid (R'), varying from about 8, to 14 carbon atoms, depending upon the particular capsaicinoid. These side chains, both saturated, and unsaturated add to the pungency of capsicums, and themselves possess antimicrobial properties of their own, without apparently contributing corrosiveness, or toxicity to vanillylamide.

Figure 4:
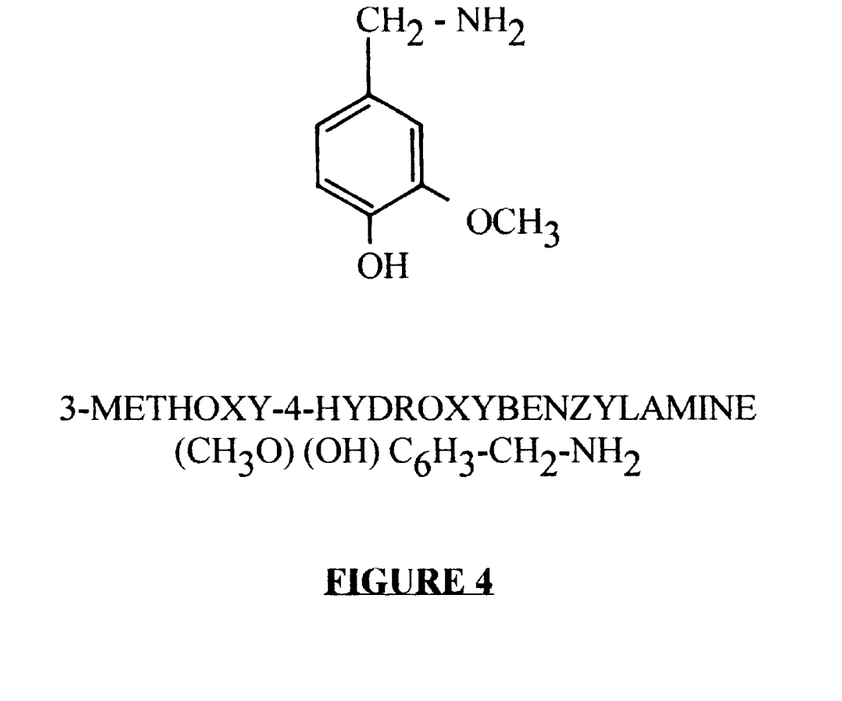
FIG. 4 is a molecular diagram of 3-methoxy-4-hydroxybenzylamine.

Hydrolysis of capsaicinoids yield active agents as well. The splitting off of the side acid chain, and it's replacement with a hydrogen (H) atom yields the primary amine vanillylamine, or 3-methoxy-4-hydroxybenzylamine (FIG. 4) from vanillylamide (FIG. 5), in the case of all capsaicinoids. Conversely, the side acid chain, receiving a hydroxy (OH) group, is converted to a fatty acid, and yields a different hydrolyte for each individual capsaicinoid. In the case of capsaicin (FIG. 6), hydrolysis of the side acid chain R' (FIG. 6) $CO-(CH_2)_4-CH=CH-(CH_3)_2$ yields isodecylenic acid $COOH-(CH_2)_4-CH=CH-CH-(CH_3)_2$.

Figure 8:
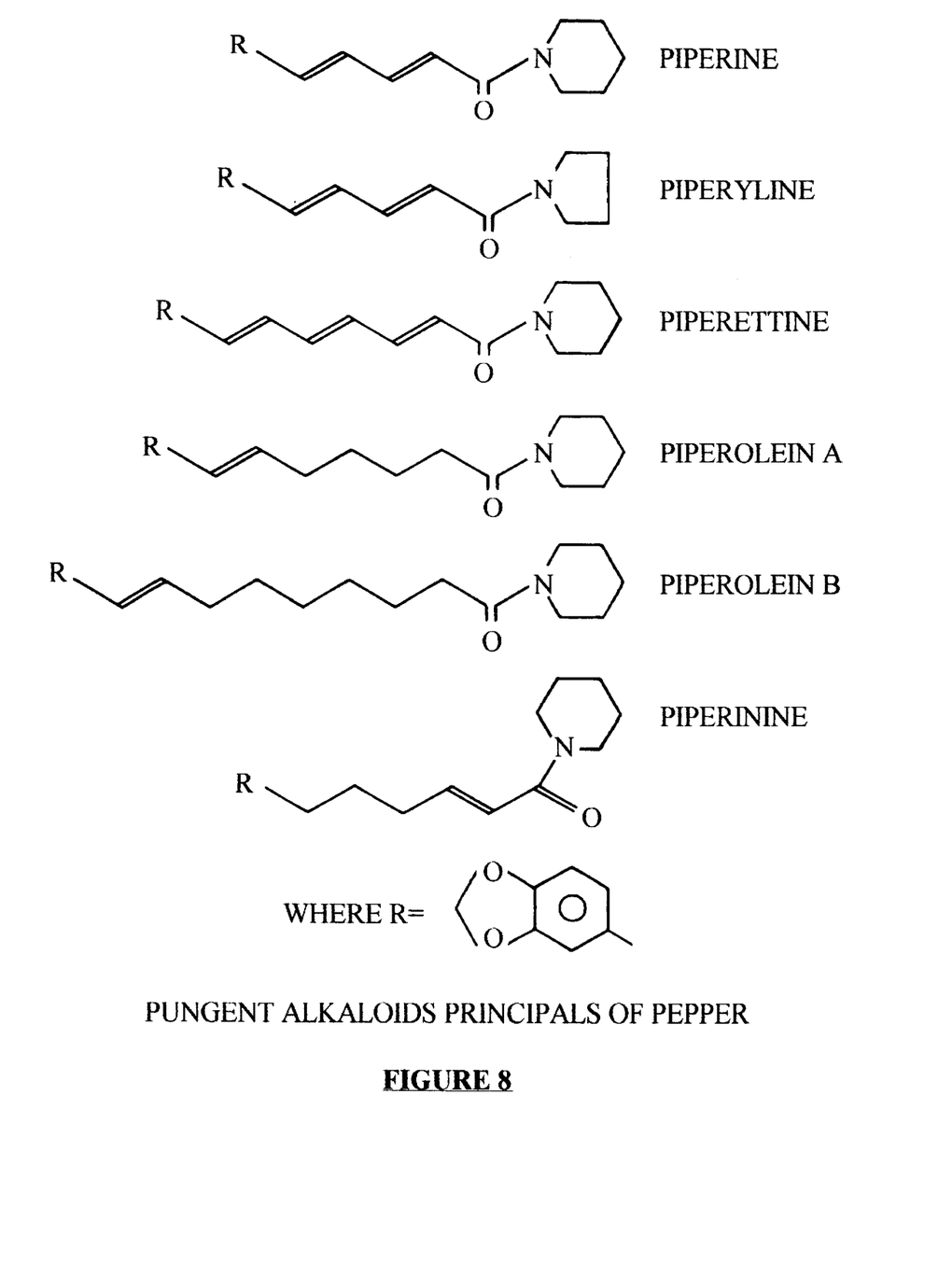
FIG. 8 is a molecular diagram of the pungent alkaloid principals of pepper.
Figure 9:
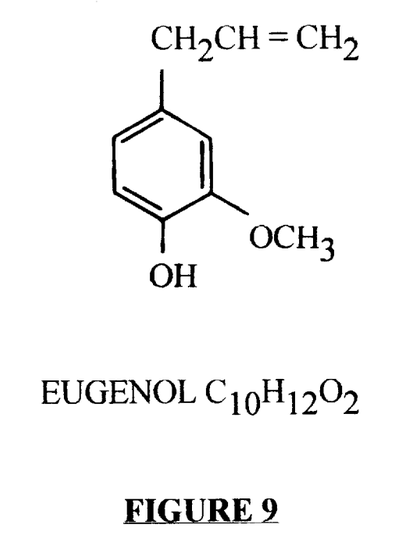
FIG. 9 is a molecular diagram of eugenol.

The piperidine series (FIGS. 7 & 8)), represent a group of analogous alkaloid compounds from which most of the pungent principals found within plants of the Piperaceae family, of which black pepper (*Piper nigrum*) is a member, are found. Also classified as acid amides, the piperidine series, like the capsaicinoids found in capsicum species, are primarily responsible for the characteristic sharp, pungent taste of black pepper.

The piperidine ring (FIG. 7) structure is diverse from that of phenol (FIG. 1). Though also a six membered, carbocyclic compound, the piperidine series instead contain one nitrogen (N) hetero atom within the ring. Piperidine is heteroparaffinic, and contains no double bonds. The hetero nitrogen atom within the ring is a contributor to the pungency of these compounds. The attachment of a hydrogen (H) atom to the hetero nitrogen atom within the ring forms the amine structure. Attachment of a hydrocarbon group, in the form of a side acid chain (R" FIG. 8) attached to a benzene structure establishes the acid amide structure. These compounds include; piperine $C_{17}H_{19}NO_3$ (FIG. 8), chavicine $C_{17}H_{19}NO_3$, piperettine $C19_{21}O3N$, piperidine $(CH_2)_5H$, piperyline, piperolein A, piperolein B, piperanine, and others.

Hydrolysis of the piperidine series, like the capsaicinoids, yield active, pungent compounds. Chavicine, for example is hydrolysed to piperidine, which receives an additional hydrogen (H) atom to form a primary amine, and chavicic acid, which receives the hydroxy (OH) group to form the fatty acid.

Hydrolysis of these capsaicinoid, and piperidine acid amides, as well as the other listed compounds may be accomplished with chemical catalysts, or by boiling a liquid preparation in water. Hydrolysis does not appear to diminish pungency, and in some applications appears to enhance both pungency, and therapeutic action.

The carbonyl group (C=O) side chain substituent, common to all the above compounds (except eugenol) is also believed to be a contributor to therapeutic action.

Other active agents found within capsicum include citric acid, vitamins A, B1, B2, C, and E, iron, potassium and niacin in significant quantities, along with other lipids, and carotenoids including capsanthin, capsorubin, and others. Vitamin C concentrations of 100 milligrams per ounce, are the highest of any natural food compound. Vitamin A content is also high, with 6170 I.U. per ounce.

An infusion of pepper is prepared by soaking approximately 4 $cm^3$ (¼ teaspoon) of commercially available ground red, or black pepper, to one liter (1 quart) of water of sensibly comfortable temperature. Set at least ten minutes before use for best results. Strain plant residue before use if desired.

A more potent tea uses about 16 $cm^3$ (1 teaspoon) of ground pepper for each liter (quart) of sensibly comfortable water. Tea may also be prepared from boiling water, or itself be boiled in water before use. Boiling pepper in water assures complete hydrolysis of the pungent principals, which are also active agents. A stronger tea would use the same amount of spice with less water, perhaps ¼ the amount above.

A tincture is prepared by soaking ground red, or black pepper in a solution containing approximately 60% ethanol, and 40% water. Pure ethanol, acetone, chloroform, vinegar (acetic acid), and others may also be used. The fluid volume of the solution may be about three, or four times that of the dry volume of the ground pepper. The mixture should be agitated, at least occasionally, over a period of at least two hours, with maximum extraction being obtained after about six hours. Allowing the mixture to sit over night produces excellent results. Strain off the residual ground pepper.

A preparation of pepper drops is obtained by reducing tincture through heat, or passive evaporation. Drops made by this method are similar in purity to some grades of commercially available oleoresin. Drops appear to concentrate by a factor of about 10 fold.

A plaster, or poultice is prepared by mixing ground pepper with water, until it has a paste-like consistency that will assure good adherence to the skin, or cloth to which it is applied.

A lotion, a cream, or a shampoo may be obtained by adding to any commercially available, shampoo, cream, or lotion, a portion of drops, or tincture equal to approximately 25% of the volume of lotion, cream, or shampoo carrier.

A douche is prepared from infusion, or tea that is strained of the plant residue material before use.

A suppository is made in cocoa butter, or gelatin in the same strength as douche, or lotion.

An injection is prepared from a purified version of infusion, tea, drops, etc., administered into tissue via hypodermic, or in a fluid stream into body cavities such as the vagina, on the cervix, uterus, rectum, mouth, and throat directly on infected areas.

A powder is pepper in ground form, or extracts mixed, and/or bound within a binding powder carrier such as talc.

A pepper impregnated fabric include clothing, and shoe liners made from capsicum wool, or any other pepper compound. For plantar warts, socks, or shoes with liners impregnated with pepper may be worn. Also undergarments, and athletic wear, or anything that has contact with infected areas of the skin including bandages.

Treatment recommendations given below are general guidelines and may be altered to suit specific conditions. If one recommended concentration appears unsuitable, the next graduation should be used.

Consideration as to area of infection, patient sensitivity to the medication and certainly how anxious the patient is to be rid of the warts. Higher concentrations seem most effective.

In the lower concentrations, an infusion may be used where skin sensitivity is high. Infusion works well as a scalp rinse, mouth rinse, a bath for the feet and skin, genital area, and as a douche, or injection.

In higher concentrations, administrations equivalent to a tincture, a powder, a poultice, and a preparation of drops are recommended where skin sensitivity will permit.

Still higher concentration drops for areas of low skin sensitivity appear most effective having produced cure of plantar warts in less than one day after one single treatment. Drops appear also to have a prophylactic action of greatest duration lasting days after application. This appears also to prevent new wart growths around the old, a common problem with prior art treatments. Drops made from cayenne pepper are extremely irritating to eyes, mucosa, and more sensitive skin such as in the crotch area, so care should be taken. Drops made from less pungent botanicals should be considered. Drops made from paprika for example, are much better tolerated, and can even be administered full strength to these sensitive areas without undue discomfort.

A tea represents a moderate concentration of pepper compounds. It may be used in the same manner as infusion. Tea may also be used in place of the higher concentration carriers, such as drops or tincture.

An injection directly into the wart to maximize treatment and minimize exposure to more sensitive surrounding tissue such as in the genital area is recommended where possible.

A lotion or shampoo may be prepared with any commonly available lotion, or shampoo, and applied to infected areas in its intended manner. Other therapeutic agents, in addition to pepper extracts, may be added to shampoo and lotion. If irritation is a concern, a topical anesthetic, such as lidocaine, or benzocaine may be added to lotion to reduce severity. If skin is very dry, emollients may also be added to lotion.

A pepper aerosol may be used in the treatment of the mouth, or throat. In this administration, care should be taken as aerosol is extremely irritating to the nose, throat, lungs, and eyes, especially when airborne. This is especially true of capsicum aerosol.

Pepper powder is also very irritating when airborne, and like aerosol, has a more limited medical application than the other carriers. If used as a foot powder for example, it is best to fix the pepper compounds within a powder binder such as talc, to prevent, or lessen escape of airborn particulate.

The unprecedented effectiveness of the current invention is demonstrated in the treatment of three patients, all infected with warts.

In the first illustration, a 12 year old boy, afflicted with a large plantar wart on the heel of his foot, in which the boy is completely healed after a single treatment with a pepper extract.

The boy has a large, brownish colored plantar wart on the upper inside portion of the heel of his right foot. For more than two years, the wart has caused the boy mild, to extreme discomfort, particularly when walking. On numerous occasions over the course of this period, the wart has been treated with several over the counter, and physician prescribed topical medications that yield no noticeable improvement in the condition. The boy is accustomed to shaving the wart off at the skin surface at regular intervals to reduce the size, and hence the degree of discomfort associated with its rapid growth. When the upper layers of the wart are removed in this manner, the remainder of the tumor appears as a cluster of milky-white stones buried below the translucent layers of skin on the heel. Regardless of these continued treatments, the wart continues to grow back causing the usual discomfort.

Prior to treatment with pepper drops, the wart is examined, and appears to occupy a brownish, rough area of the heal approximately 25 mm. (1") in diameter at the base. The central portion is raised, forming a nodule approximately 6 mm. (¼") above the skin surface.

The wart is treated topically with one (1) drop of pepper drops that were prepared from a standard 4:1 red pepper acetone tincture that was reduced 40 times by room temperature evaporation. Upon application, the boy reports no notable sensation from the treatment.

Eight weeks after this single treatment, the boy's heel is again examined, and to the astonishment of the boy and his mother the wart is completely disappeared! Close examination of the entire foot shows no evidence of warts. The previously infected area of skin looks perfectly normal and healed, with no trace of disease, or abnormality.

When asked about details of the course of healing of the wart, the boy replied that after treatment with the pepper drops, he had experienced no further discomfort in the area of the wart. This lack of discomfort caused him to forget about the wart, and he had not looked at it since treatment. It has been many months at this writing since the boy's treatment. The wart has not returned, nor have new ones arisen.

In a second illustration, a ten-year old girl afflicted with two plantar warts on the great toe is completely healed after less than ten treatments with a pepper extract.

The girl has two spotted, dark, brownish-colored plantar warts, approximately 5 mm (⅛") in diameter on the upper, and lower inside edge of the great toe of the right foot. Each waft is surrounded with a raised callus. For the preceding few weeks, the wart has caused the girl increasing discomfort, particularly when walking. The girl was received no prior treatment for the wart.

Each wart is then brushed lightly with a cotton swab dipped in pepper drops prepared from a standard 4:1 red pepper acetone tincture that was reduced 40 times by room temperature evaporation. This procedure is repeated every day or two over the course of several, days. The girl reports no notable sensation from treatment.

On the second day just prior to a second treatment, the warts are again examined. Each wart appears to have reduced in size, and taken on a darker, more distinctive appearance. When asked about walking discomfort due to the wart, the girl replied that she had not noticed any discomfort since the first treatment on the previous day.

Prior to each subsequent treatment, the girl is again asked if she has noticed any discomfort due to the wart. On each occasion, she states she has felt no discomfort at all since before the first treatment.

On the morning of the eighteenth day from the first treatment, the girl's toe is again examined. The wart on the upper part of the toe has disappeared, leaving a cup shaped indentation in its place. The remaining wart on the lower portion of the toe is then treated. Late in the afternoon, the toe is again examined only to reveal that the wart on the lower portion of the toe has likewise disappeared, leaving a similar cup shaped indentation in it's place as with the other wart. The girl's sock is then inverted and shaken, only to have the wart fall out on a table surface.

Subsequent examinations of the girl's toe over a period of days reveal a gradual reduction and eventual disappearance of the indentations, and calluses to where the skin appears perfectly healthy, with no evidence whatsoever of the prior wart or callus remaining. The girl is completely healed. After more than 30 months of observation, the girl has yet to have the warts return, or new ones emerge anywhere on the body.

In a third illustration, a seven-year old boy afflicted with a plantar wart on the great toe is completely healed in one day, after one single treatment with a pepper extract.

The boy has a spotted, dark brownish-colored plantar wart, approximately 5 mm (⅛") in diameter on the lower inside edge of the great toe of the left foot. The wart is surrounded with a raised callus. For the preceding weeks, the wart has caused the boy increasing discomfort, particularly when walking. The boy was received no prior treatment for the wart.

A single drop of pepper drops prepared from a standard 4:1 red pepper acetone tincture that was reduced 40 times by room temperature evaporation was placed directly on the wart using an eyedropper. A section of clear adhesive tape is placed over the treated wart to avoid contact with the socks, and fingers. The boy reports no notable sensation from treatment. The boy puts his socks and shoes on, and leaves for school that morning.

That afternoon after returning home from school, the boy's shoe and sock are removed for inspection, only to find a cup shaped indentation in place of where the wart had been. The tape was also missing. When asked, the boy explained that during afternoon recess, he had removed his shoe, sock, the tape, and lifted the wart out of the skin himself. When asked if the wart was hurting, the boy said no, that he removed the wart "because it was wiggley". When asked if it hurt, or bled to remove the wart, the boy said "no, it didn't hurt or bleed; it came out real easy".

Subsequent examinations of the boy's toe over a period of days reveal a gradual reduction and eventual disappearance of the indentation, and callus. The skin returns to a perfectly healthy condition, with no evidence whatsoever of the prior wart or callus remaining. The boy is completely healed. After more than 20 months of observation, the boy has yet to have the wart return, or new ones emerge anywhere on the body.

While my above description includes many be regarded as limitations as an exemplification of specificities, these should not on the invention, but rather certain preferred embodiments. Accordingly, the scope of the invention should not be determined by these illustrated embodiments, but by the appended claims, and their legal equivalents.

I claim:

1. A method of treating papillomas comprising:
   Administration to the papilloma a suitable carrier containing a primary therapeutic agent obtainable from pepper, or an equivalent in a therapeutically effective concentration.

2. A method of treating papillomas comprising:
   Administration to the papilloma a suitable carrier containing as a primary therapeutic agent an antifungal medication in a therapeutically effective concentration.

3. The method of claim 1, further comprising villous papillomas.

4. The method of claim 1, wherein the papillomas include polyps.

5. The method of claim 1, wherein the papillomas include warts.

6. The method of claim 1, wherein the papillomas include common warts.

7. The method of claim 1, wherein the papillomas include plantar warts.

8. The method of claim 1, wherein the papillomas include genital warts.

9. The method of claim 1, wherein said administration is by injection.

10. The method of claim 1, wherein said agent is a capsaicinoid analog.

11. The method of claim 1, wherein said agent has a piperidine constituent.

12. The method of claim 1, wherein said pepper is cayenne pepper.

13. The method of claim 1, wherein said pepper is paprika.

14. The method of claim 1, wherein said pepper is piperaceous.

15. The method of claim 1, wherein said pepper is black pepper.

16. The method of claim 1, wherein said equivalent is a synthetic.

17. The method of claim 1, wherein said concentration is equivalent to oleoresin or greater.

18. The method of claim 1, wherein said concentration is equivalent to a tincture or greater.

19. The method of claim 1, wherein said concentration is equivalent to a lotion or greater.

20. The method of claim 1, wherein said concentration is equivalent is a lotion or less.

21. The method of claim 2, further comprising villous papillomas.

22. The method of claim 2, wherein the papillomas include polyps.

23. The method of claim 2, wherein the papillomas include warts.

24. The method of claim 2, wherein the papillomas include common warts.

25. The method of claim 2, wherein the papillomas include plantar warts.

26. The method of claim 2, wherein the papillomas include genital warts.

27. The method of claim 2, wherein said administration is by injection.

28. The method of claim 2, wherein said medication is amphotericin B.

29. The method of claim 2, wherein said medication has an azole constituent.

30. The method of claim 2, wherein said medication has a triazole constituent.

31. The method of claim 1, further comprising animal papillomas.

32. The method of claim 31, wherein said animal is livestock.

33. The method of claim 31, wherein said animal is a pet.

34. The method of claim 31, wherein said animal is a companion animal.

35. The method of claim 2, further comprising animal papillomas.

36. The method of claim 35, wherein said animal is livestock.

37. The method of claim 35, wherein said animal is a pet.

38. The method of claim 35, wherein said animal is a companion animal.

* * * * *